United States Patent [19]
Kempen

[11] Patent Number: 5,854,238
[45] Date of Patent: Dec. 29, 1998

[54] USE OF A THIENOTRIAZOLODIAZEPHINE TO INCREASE APOLIPOPROTEIN A-I LEVELS

[75] Inventor: Herman Kempen, Allschwil, Switzerland

[73] Assignee: Hoffmann-La Roche Inc., Nutley, N.J.

[21] Appl. No.: 11,819

[22] PCT Filed: Aug. 30, 1996

[86] PCT No.: PCT/EP96/03814

§ 371 Date: Feb. 23, 1998

§ 102(e) Date: Feb. 23, 1998

[87] PCT Pub. No.: WO97/09048

PCT Pub. Date: Mar. 13, 1997

[30] Foreign Application Priority Data

Sep. 9, 1995 [EP] European Pat. Off. .............. 95114163

[51] Int. Cl.[6] .................................................. A61K 31/505
[52] U.S. Cl. .......................................................... 514/220
[58] Field of Search ............................................... 514/220

[56] References Cited

U.S. PATENT DOCUMENTS 4,155,913  5/1979  Hellerbach et al. ................ 260/308 R

FOREIGN PATENT DOCUMENTS 2405682   8/1974  Germany .
50100096  8/1975  Japan .

OTHER PUBLICATIONS

Tahara et al., Chem. Pharm. Bull., 35(5), 2119–21 (abstract), 1987.
Kwiterovich et al., Am J. Cardiology, 69:1015–21, Apr. 15, 1992.

*Primary Examiner*—Phyllis G. Spivack
*Attorney, Agent, or Firm*—George W. Johnston; William H. Epstein; John P. Parise

[57] ABSTRACT

9-methyl-4-phenyl-6H-thieno[3,2-f]-s-triazolo[4,3-a][1,4] diazepine for the treatment and prevention of illnesses which are caused by low plasma apolipoprotein A-I levels as coronary coronary disease.

16 Claims, No Drawings

USE OF A THIENOTRIAZOLODIAZEPHINE TO INCREASE APOLIPOPROTEIN A-I LEVELS

This application is a 371 of PCT/EP96/03814 filed Aug. 30, 1994.

The invention is based on the finding of novel physiological properties of the compound 9-methyl-4-phenyl-6H-thieno[3,2-f]-s-triazolo[4,3-a][1,4]-diazepine, hereinafter Compound C.

Compound C and its preparation are described in U.S. Pat. No. 4,155,913. This patent also describes analogs of Compound C and contains data showing the anticonvulsant and muscle relaxant activity of one of these analogs.

It has now been found that Compound C is active in increasing plasma apolipoprotein A-I (apo A-I). Apo A-I is a major protein constituent of plasma high density lipoproteins (HDL). Low plasma levels of HDL are known to be associated with an increased incidence of coronary artery disease (CAD). The same applies to both low plasma levels of apo A-I and high levels of apolipoprotein B (apo B); J. of Biol. Chem. 264: 6488–6494, 1989; Mayo Clin. Proc. 61: 313–320, 1986; New England J. of Medicine 325: 373–381, 1991; Am. J. Cardiol. 69: 1015–1021, 1992; J. Am. College Cardiol. 19: 792–802, 1992.

In one aspect, the present invention relates to the use of Compound C for the manufacture of medicaments for the treatment and prevention of illnesses which are caused by low plasma apo A-I levels. Examples of such illnesses are the above mentioned CAD, mainly myocardial infarction, and atherosclerosis.

In a further aspect the invention relates to plasma apo A-I levels enhancing medicaments which contain Compound C as the active ingredient, as well as to a process for the manufacture of such medicaments, which process comprises bringing Compound C and, if desired, one or more other therapeutically valuable substances into a galenical administration form.

In an other aspect the invention relates to a method of increasing plasma apo A-I levels in mammals, particularly human beings, which method comprises administering an effective amount of Compound C.

The activity of Compound C on plasma levels of apo A-I can be demonstrated by standard methods. For example, male hamsters were fed a coco-nut enriched diet. Ten controls and five drug treated animals were used. Compound C was given mixed with the food at a daily dose of 30 mg/kg for 10 days. The experiment was conducted as described in J. Lipid Res. 36: 1567–1585, 1995. For each of the plasma parameters apo A-I, apo B and triglycerides, the mean concentrations in g/L or mg/dl at both day-1 and day 10 of the assay are as follows:

| Plasma parameter: | Control: | | Compound C: | |
|---|---|---|---|---|
| | day-1 | day 10 | day-1 | day 10 |
| apo A–I (g/L) | 1.00 ± 0.08 | 0.97 ± 0,09 | 0.91 ± 0.08 | 1.30 ± 0.15* |
| apo B (g/L) | 0.79 ± 0.09 | 1.20 ± 0.19* | 0.84 ± 0.11 | 1.20 ± 0.35* |
| triglycerides (mg/dl) | 312 ± 46 | 288 ± 34** | 197 ± 23 | 307 ± 19** |

*significantly different (p < 0.05 paired t-test) as compared to day-1
**not significantly different as compared to day-1

The results show that the administration of Compound C results in an increase over the control group of the apo A-I level without significantly affecting the apo B and triglycerides levels.

The administration of Compound C did not induce any manifest adverse effect. The animals remained healthy, lively, kept eating and growing at normal rates and were not showing any signs of sedation.

Compound C can be used as active ingredient in pharmaceutical preparations. The pharmaceutical preparations are administered orally, e.g. in the form of tablets, coated tablets, dragées, hard and soft gelatine capsules, solutions, emulsions or suspensions. The active ingredient can be mixed with pharmaceutically inert, inorganic or organic carriers in order to manufacture such preparations. Lactose, corn starch, talc, stearic acid or its salts can be used, for example, as carriers for tablets, coated tablets, dragées and hard gelatine capsules. Suitable carriers for soft gelatine capsules are, for example, vegetable oils, waxes or fats; depending on the nature of the active ingredient no carriers are, however, usually required in the case of soft gelatine capsules. Suitable carriers for the manufacture of solutions and syrups are, for examples, water, saccharose, invert sugar and glucose. The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

As mentioned earlier, Compound C can be used in the control or prevention of illnesses such as atherosclerosis and CAD, particularly myocardial infarction. The dosage can vary within wide limits and will, of course, be fitted to the individual requirements in each particular case. In general, an oral daily dosage of about 10 mg to about 1 g, preferably of about 100 to about 500 mg, should be sufficient. The daily dosage can be taken in one, two or three single doses, e.g. with food. A single dosage form contains from about 10 to 500 mg of Compound C.

A hard gelatine capsule contains e.g. 30, 60, 125, 250 or 500 mg of Compound C and finely crystalline lactose to a final fill weight of 580–590 mg.

I claim:

1. A method for preventing coronary artery disease which comprises administering an effective amount of the compound 9-methyl-4-phenyl-6H-thieno[3,2-f]-s-triazolo[4,3-a][1,4]diazepine to an individual not afflicted with coronary artery disease.

2. The method of claim 1, wherein the coronary artery disease is atherosclerosis.

3. The method of claim 1, wherein the coronary artery disease is myocardial infarction.

4. The method of claim 1, wherein the administering comprises orally delivering a daily dosage of 9-methyl-4-phenyl-6H-thieno[3,2-f]-s-triazolo[4,3-a][1,4]diazepine in an amount from about 10 mg to about 1 g per day.

5. The method of claim 4, wherein the administering comprises orally delivering a daily dosage of 9-methyl-4-phenyl-6H-thieno[3,2-f]-s-triazolo[4,3-a][1,4]diazepine in an amount from about 100 mg to about 500 mg per day.

6. The method of claim 4, wherein the administering is performed once a day.

7. The method of claim 4, wherein the administering is performed twice a day.

8. The method of claim 4, wherein the administering is performed three times a day.

9. A method for treating coronary artery disease which comprises administering an effective amount of the compound 9-methyl-4-phenyl-6H-thieno[3,2-f]-s-triazolo[4,3-a][1,4]diazepine to an individual afflicted with coronary artery disease.

10. The method of claim 9, wherein the coronary artery disease is atherosclerosis.

11. The method of claim 9, wherein the coronary artery disease is myocardial infarction.

12. The method of claim 9, wherein the administering comprises orally delivering a daily dosage of 9-methyl-4-phenyl-6H-thieno[3,2-f]-s-triazolo[4,3-a][1,4]diazepine in an amount from about 10 mg to about 1 g per day.

13. The method of claim 12, wherein the administering comprises orally delivering a daily dosage of 9-methyl-4-phenyl-6H-thieno[3,2-f]-s-triazolo[4,3-a][1,4]diazepine in an amount from about 100 mg to about 500 mg per day.

14. The method of claim 12, wherein the administering is performed once a day.

15. The method of claim 12, wherein the administering is performed twice a day.

16. The method of claim 12, wherein the administering is performed three times a day.

* * * * *

UNITED STATES PATENT AND TRADEMARK OFFICE
CERTIFICATE OF CORRECTION

PATENT NO. : 5,854,238
DATED : December 29, 1998
INVENTOR(S) : Herman Kempen

It is certified that error appears in the above-identified patent and that said Letters Patent is hereby corrected as shown below:

Title page, column 1, at [54] in the title, delete "THIENOTRIAZOLODIAZEPHINE" and insert -- THIENOTRIAZOLODIAZEPINE --

Signed and Sealed this

Fourth Day of May, 1999

Attest:

Attesting Officer

Q. TODD DICKINSON

Acting Commissioner of Patents and Trademarks